United States Patent
Chen et al.

(10) Patent No.: US 10,709,790 B2
(45) Date of Patent: Jul. 14, 2020

(54) CHEMICAL CONJUGATES OF EVANS BLUE DERIVATIVES AND THEIR USE IN THE PRODUCTION OF LONG-ACTING THERAPEUTICS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Xiaoyuan Chen, Potomac, MD (US); Lixin Lang, North Potomac, MD (US); Gang Niu, Rockville, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 15/735,687

(22) PCT Filed: Jun. 21, 2016

(86) PCT No.: PCT/US2016/038475
§ 371 (c)(1),
(2) Date: Dec. 12, 2017

(87) PCT Pub. No.: WO2016/209795
PCT Pub. Date: Dec. 29, 2016

(65) Prior Publication Data
US 2019/0201537 A1    Jul. 4, 2019

Related U.S. Application Data

(60) Provisional application No. 62/182,694, filed on Jun. 22, 2015.

(51) Int. Cl.
| | | |
|---|---|---|
| A61K 47/54 | (2017.01) | |
| A61P 3/10 | (2006.01) | |
| A61K 38/12 | (2006.01) | |
| C07D 207/24 | (2006.01) | |
| A61K 47/64 | (2017.01) | |

(52) U.S. Cl.
CPC .............. $A61K\ 47/54$ (2017.08); $A61K\ 38/12$ (2013.01); $A61K\ 47/643$ (2017.08); $A61P\ 3/10$ (2018.01); $C07D\ 207/24$ (2013.01)

(58) Field of Classification Search
None
See application file for complete search history.

(56) References Cited

U.S. PATENT DOCUMENTS

| 7,368,099 B2 | 5/2008 | Katayama |
| 2016/0287730 A1 | 10/2016 | Chen et al. |
| 2019/0084931 A1 | 3/2019 | Chen et al. |

FOREIGN PATENT DOCUMENTS

| CN | 103242255 A | 8/2013 |
| CN | 104650217 A | 5/2015 |
| WO | 2004075925 A1 | 9/2004 |
| WO | 2006025304 A1 | 3/2006 |
| WO | 2017192874 A1 | 11/2017 |
| WO | 2017196806 A1 | 11/2017 |
| WO | 2019070236 A1 | 4/2019 |
| WO | 2019165200 A1 | 8/2019 |

OTHER PUBLICATIONS

International Preliminary Report on Patentability dated Dec. 26, 2017; International Application No. PCT/US2016/038475; International Filing Date Jun. 21, 2016 (7 pages).
Haojun Chen et al., "Novel molecular 'add-on' based on Evans Blue confers superior pharmacokinetics and transforms drugs to theranostic agents", Journal of Nuclear Medicine, vol. 58, No. 4, Nov. 22, 2016, 10 pages.
Satheesh Chandran M. et al., "Preparation and Characterization of Chain-Extended Bismaleimide/Carbon Fibre Composites" Hindawi Publishing Corporation, International Journal of Polymer Science, vol. 2010, 2010, 9 pages.

(Continued)

*Primary Examiner* — Kamal A Saeed
(74) *Attorney, Agent, or Firm* — Cantor Colburn LLP

(57) ABSTRACT

The present invention is directed to a compound of Formula I or Formula II or a pharmaceutically acceptable ester, amide, solvate, or salt thereof, or a salt of such an ester or amide or a solvate of such an ester amide or salt: Formula I Formula II The compounds of Formula I may be covalently bonded to a therapeutic compound or fragment thereof to provide a compound of Formula II and thereby extend the half-life of the therapeutic compound. The invention is also directed to pharmaceutical compositions of the disclosed compounds, as well as their use in the diagnosis or treatment of diseases.

Formula I

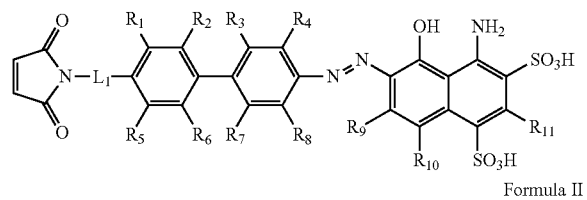

Formula II

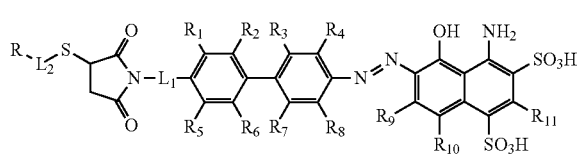

33 Claims, 10 Drawing Sheets

(56) References Cited

OTHER PUBLICATIONS

Zhibo Liu et al., "Simple bioconjugate chemistry serves great clinical advances: albumin as a versatile platform for diagnosis and precision therapy", Chemical Society Reviews, vol. 45, No. 5, Mar. 7, 2016, 48 pages.
Chen, H. et al., "Chemical Conjugation of Evans Blue Derivative" Theranostics (2016) vol. 6, No. 2, p. 243-253.
International Search Report of International Application No. PCT/US2016038475; dated Aug. 16, 2016; 6 pages.
Kaspar, A., Reicher, J., "Future directions for peptide therapeutics development" Drug Discovery Today (2013) vol. 18, No. 17, p. 807-817.
Liu Y. et al., "Stable Evans Blue Derived Exendin-4 Peptide for Type 2 Diabetes Treatment" Bioconjugate Chemistry (2016) vol. 27, p. 54-58.
Niu, G. et al., "In Vivo Labeling of Serum Albumin for PET" The Journal of Nuclear Medicine (2014), vol. 55, No. 7, p. 1150-1156.
Wang, Y. et al., "In vivo albumin labeling and lymphatic imaging" PNAS (2015) vol. 112, No. 1, p. 208-213.
Written Opinion of the International Searching Authority for International Application No. PCT/US2016/038475; dated Aug. 16, 2016; 7 pages.
Extended European Search Report issued in EP Application No. 17796666.0 dated Oct. 10, 2019, 5 pages.

Panel A

Panel B

CHEMICAL CONJUGATES OF EVANS BLUE DERIVATIVES AND THEIR USE IN THE PRODUCTION OF LONG-ACTING THERAPEUTICS

CROSS REFERENCE TO RELATED APPLICATION

This application is a national stage application of PCT/US2016/038475 filed Jun. 21, 2016, which claims priority to provisional U.S. Patent Application No. 62/182,694 filed Jun. 22, 2015, both of which are hereby incorporated by reference in their entireties.

STATEMENT OF GOVERNMENT SUPPORT

This invention was made in part with government support from the National Institutes of Health. The government has certain rights in this invention.

BACKGROUND OF THE INVENTION

Field of the Invention

The present invention relates to functionalized derivatives of Evans Blue dye, and more particularly to functionalized derivatives of Evans Blue dye that extend the half-life of therapeutic compounds.

Brief Description of the Art

The effectiveness of pharmaceuticals depends heavily on pharmacokinetics. In particular, compounds for pharmaceutical use must have sufficient half-life to exert the desired effect on the patient. Various approaches have been used to increase the half-life of pharmaceutical compounds in the body. One method of increasing half-life is to reduce the rate of clearance of the drug from the body, which can be done by inhibition of clearance mechanisms, either through direct modification of the drug, or by addition of other agents which act on the clearance pathways. Reduction of clearance is particularly desired for protein drugs, as they are highly vulnerable to degradation by proteases.

As the kidney generally filters out molecules below 60 kDa, one method of clearance rate reduction is to increase the molecular size of the protein drug through, for example, protein fusions, glycosylation, or the addition of polyethylene glycol polymers (PEG). However, some of these approaches have disadvantages. For example, one common strategy to improve the pharmacokinetics of pharmaceutical agents is to attach poly(ethylene glycol) (PEG) moieties to therapeutic compounds, a process known as PEGylation. However, the covalent attachment of PEG to a drug or therapeutic protein can mask the agent from the host's immune system to reduce immunogenicity and antigenicity, and increase the hydrodynamic size of the agent which prolongs its circulatory time by reducing renal clearance. PEGylation can also provide water solubility to hydrophobic drugs and proteins. However, due to the bulky size of PEG chain, the biological activity is inevitably comprised after PEGylation.

For diabetes treatment, several drugs have been developed by conjugating a lipid chain to either insulin or GLP-1 to increase their circulation time. Although lipid acid can bind with albumin to protect the sensitive peptides, the biodistribution is still not optimal since a high percentage of administered drug will be accumulated in liver and subjected to degradation. In addition, the lipophilicity of the complex also increases the difficulty of chemical reaction and production.

Fusion of protein drugs with large proteins such as albumin or the Fc domain of immunoglobulin G (IgG) can increase drug half-life by increasing the molecular size of the drug and in turn reducing renal clearance. In addition to increasing size, fusion with either albumin or the IgG Fc domain adds functionality to the fused complex and enables interaction with the neonatal Fc receptor (FcRn), which salvages bound ligands from intracellular catabolism by recycling them back to circulation. This interaction with FcRn contributes to the extraordinarily long 21 day serum half-life of albumin and IgG in humans. Therefore, engineering proteins to interact with serum IgG has the potential to significantly increase half-life by reducing both renal clearance and intracellular catabolism. Through these methods the in vivo exposure of the polypeptide or protein therapeutics can be extended. Small molecule drugs may also improve their in vivo pharmacokinetics by association with various plasma components.

As the most abundant protein in blood plasma (around 50 mg/ml), human serum albumin (HSA) with a molecular weight of 66.5 kDa is the chief carrier protein in the blood. It acts as the chief solubilizing agent for long chain fatty acids, a detoxifying protein through its binding of bilirubin, and the transport vehicle for heavy metal ions in the blood. Since the mid-1990s albumin has been studied as a carrier protein, either for targeting drugs to inflamed or malignant tissue or for extending their half-life. Two principal albumin-based technologies have been developed for therapeutic use. One method is to pass lipophilic drugs and HSA under high pressure through a jet to form albumin-drug nanoparticles. The other is to develop albumin-binding peptides or prodrugs that bind in situ to circulating albumin, either covalently or non-covalently, after intravenous injection.

Due to the extreme abundance in the blood circulation, albumin has advantages over immunoglobulin G (IgG) as the drug carrier. Taking drug release into consideration, physical binding is preferred to covalent binding since there is a need for a balance between albumin binding affinity and efficient drug release from the binding. To make a prodrug covalently bind to albumin, the cysteine-34 position of albumin is commonly used, since the free thiol group of cysteine-34 is a unique feature of an extracellular protein and accounts for approximately 90% of the thiol concentration in blood plasma. For example, the first and most advanced prototype of these types of prodrugs is the (6-maleimidocaproyl)hydrazone derivative of doxorubicin (DOXO-EMCH), an acid-sensitive prodrug of doxorubicin that is rapidly and selectively bound to the cysteine-34 position of endogenous albumin after intravenous administration. Aldoxorubicin contains an acid-sensitive hydrazone linker allowing doxorubicin to be released either extracellularly in the slightly acidic environment often present in tumor tissue or intracellularly in acidic endosomal or lysosomal compartments after cellular uptake of the albumin conjugate by the tumor cell.

One example of physical interaction with albumin is the development of Levemir® (Novo Nordisk), an insulin analog for treating diabetes, in which myristic acid (tetradecanoic acid) is bound to the lysine amino acid at position B29. The fatty acid on the Levemir attach to serum albumin makes it a long-acting form of insulin. Besides insulin administration, another other option of controlling glucose levels in diabetes is to stimulate insulin secretion. The peptide hormone GLP-1-(7-37) results from selective cleavage of the proglucagon molecule and increases insulin secretion in pancreatic cells but only has a half-life of 1.5-2 min due to degradation by ubiquitous enzymes. In analogy to Levemir®, GLP-1-(7-37) is derivatized with a fatty acid, for example palmitic acid, at the ε-amino position of lysine introduced at the N-terminal position of glutamic acid in the GLP-1 peptide sequence. The resulting new drug liraglutide (Victoza®) is an albumin-binding derivative of GLP-1 stable against metabolic degradation due to albumin-binding, and has a plasma half-life of 11-15 h after subcutaneous administration. Additional examples of anti-diabetic peptides modified for better drug-like properties are disclosed by Kaspar, et al. "Future Directions for Peptide Therapeutics Development", *Drug Discovery Today*, 18(17):807-817 (2013).

Albumin-based drug delivery systems are not only important treatment options for metabolic disorders such as diabetes but are also useful for cancer therapy. Using albumin as a drug carrier has several unique advantages for drug delivery to solid tumors. First, albumin-based drug carriers offer enhanced permeability and retention of macromolecules in relation to passive tumor targeting (EPR effect). Moreover, two albumin-binding proteins were found to be overexpressed in tumor environment including the gp60 receptor on tumor endothelium and SPARC, a secreted glycoprotein with high binding affinity to albumin in the tumor interstitium. Besides the EPR effect, the interplay of two albumin-binding proteins facilitates the uptake and retention of albumin in the tumor.

Evans Blue (EB) is an azo dye with a high affinity for serum albumin. It is frequently used in the measurement of blood volume, but it can also be used to show permeability to macromolecules. Because EB strongly binds to albumin, it can serve as a marker of where the large albumin molecules are localized, and thus it can be used to assess permeability of barriers, such as of the blood-brain barrier (BBB). Because albumin cannot cross the BBB and virtually all EB is bound to albumin, EB will only enter the CNS if the BBB has been compromised. EB has also been used in a viability assay, as the EB bound to albumin will enter damaged or non-viable cells, but not healthy cells.

Derivatives of Evans Blue dye are known in the art. For example, Chinese patent CN103242255 to Zhang, et al. discloses imaging agents in which a truncated version of EB which binds to albumin is linked with a macrocyclic chelating group (NOTA, 1,4,7-triazacyclononane-N,N',N''-triacetic acid) that can bind a radionuclide or other labels. Such derivatives made with macrocyclic chelating groups make an agent useful in blood pool imaging. Similarly, International patent application WO2004075925 to Katayama et al. discloses an agent useful for imaging of an exfoliated vascular endothelial site in which a truncated version of EB which binds to albumin is linked to a linear chelating group that binds to a radionuclide. The synthesis and use of EB-NOTA has been disclosed (see Niu et al., "In Vivo Labeling of Serum Albumin for PET", *J. Nucl. Med.* 55:1150-1156 (2014)).

Because of the broad potential for albumin-based therapeutics, there is a need for improved drug-albumin conjugates. The present invention is believed to be an answer to that need.

SUMMARY OF THE INVENTION

In one aspect, the present invention is directed to a compound of Formula I or a pharmaceutically acceptable ester, amide, solvate, or salt thereof, or a salt of such an ester or amide or a solvate of such an ester amide or salt:

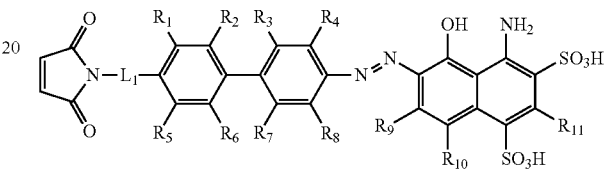

Formula I wherein:
$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy; and $L_1$ is —$(CH_2)_m$— wherein m is an integer from 0 to 12, wherein each $CH_2$ can be individually replaced with —O—, —NH(CO)—, or —(CO)NH—, providing no two adjacent $CH_2$ groups are replaced, and wherein $L_1$ is optionally substituted with 1 substituent -A-B—X, wherein A is a bond, —NH—, —NH(CO)—, —(CO)NH—, B is $C_{0-12}$alkyl, or phenyl$C_{0-12}$alkyl, and X is a hydrogen, halogen or an Sn derivative.

In another aspect, the present invention is directed to a compound of Formula II or a pharmaceutically acceptable ester, amide, solvate, or salt thereof, or a salt of such an ester or amide or a solvate of such an ester amide or salt:

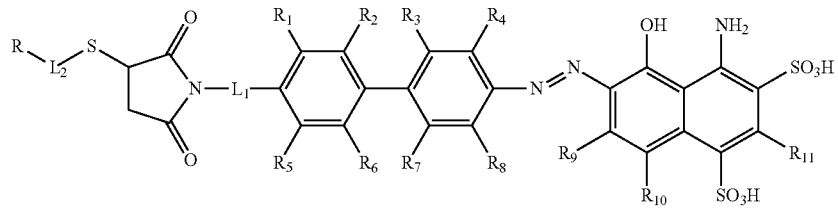

Formula II wherein:
$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy;

$L_1$ is —$(CH_2)_m$— wherein m is an integer from 0 to 12, wherein each $CH_2$ can be individually replaced with —O—, —NH(CO)—, or —(CO)NH—, providing no two adjacent $CH_2$ groups are replaced, and wherein $L_1$ is optionally substituted with 1 substituent -A-B—X, wherein A is a bond, —NH—, —NH(CO)—, —(CO)

NH—, B is $C_{0-12}$alkyl, or phenyl$C_{0-12}$alkyl, and X is a hydrogen, halogen or an Sn derivative;

$L_2$ is —(CH$_2$)$_r$— wherein r is an integer from 0 to 12, wherein each CH$_2$ can be individually replaced with —O—, —NH(CO)—, or —(CO)NH—, providing no two adjacent CH$_2$ groups are replaced; and R is a therapeutic compound.

In yet another aspect, the present invention is directed to a pharmaceutical composition comprising the compound of Formula II together with a pharmaceutically acceptable carrier.

In yet another aspect, the present invention is directed to a method of treating or diagnosing diabetes in a mammal, comprising administering to said mammal a therapeutically effective amount of a compound of Formula II, optionally in combination with one or more additional active ingredients.

These and other aspects will become apparent upon reading the following detailed description of the invention.

BRIEF DESCRIPTION OF THE DRAWINGS

The following description of the invention will be better understood when taken in conjunction with the following drawings in which.

DETAILED DESCRIPTION OF THE INVENTION

Terminology

Figure 1:
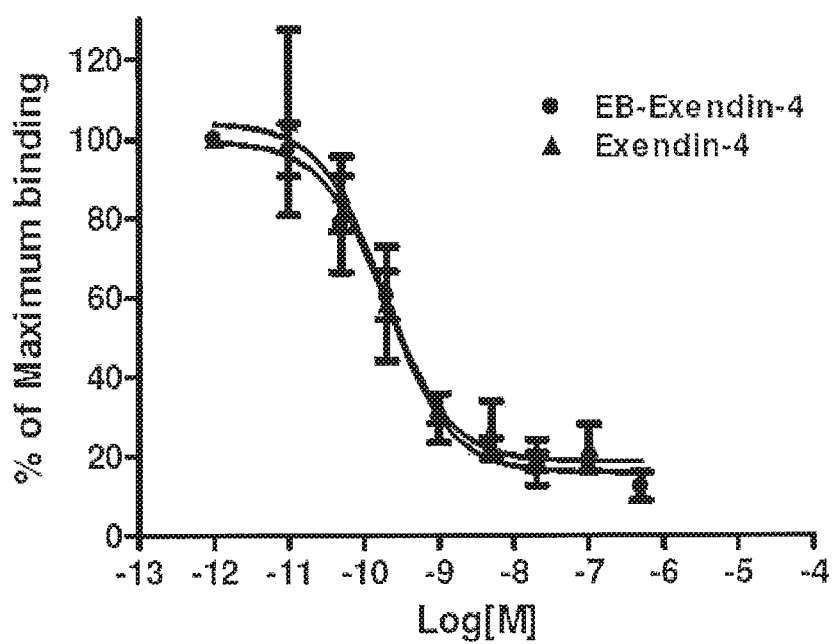
FIG. 1 is a graph showing the results of a cell binding assay of Exendin-4 and EB-Exendin-4 with INS-1 cells.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or." The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

Formulae I and II include all pharmaceutically acceptable salts of Formulae I and II.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. The term $C_0$-$C_{12}$alkyl as used herein indicates an alkyl group that can have from 1 to 12 carbon atoms or can be absent (when it is a $C_0$ alkyl group). Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—). Similarly, "alkenyloxy", "alkynyloxy", and "cycloalkyloxy" refer to alkenyl, alkynyl, and cycloalkyl groups, in each instance covalently bound to the group it substitutes by an oxygen bridge (—O—).

"Halo" or "halogen" means fluoro, chloro, bromo, or iodo.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Pharmaceutical compositions" means compositions comprising at least one active agent, such as a compound or salt of Formula II, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "therapeutically effective amount" of a pharmaceutical composition means an amount effective, when administered to a patient, to provide a therapeutic benefit such as an amelioration of symptoms, decrease disease progression, or cause disease regression.

A "therapeutic compound" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where $p<0.05$.

Chemical Description

Compounds of Formulae I and II may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound, and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth, Editors, Wiley-VCH, 2002.

As indicated above, in one aspect the present invention encompasses chemical conjugates of Evans Blue dye having the compound of Formula I illustrated below, or a pharmaceutically acceptable ester, amide, solvate, or salt thereof, or a salt of such an ester or amide or a solvate of such an ester amide or salt:

In Formula I, the substituents $R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy.

Formula I may also include linking group $L_1$ having the structure —$(CH_2)_m$— wherein m is an integer from 0 to 12, and wherein each $CH_2$ can be individually replaced with —O—, —NH(CO)—, or —(CO)NH—, providing no two adjacent $CH_2$ groups are replaced, and wherein $L_1$ is optionally substituted with 1 substituent -A-B—X, wherein A is a bond, —NH—, —NH(CO)—, —(CO)NH—, B is $C_{0-12}$alkyl, or phenyl$C_{0-12}$alkyl, and X is a hydrogen, halogen or an Sn derivative.

In an embodiment of Formula I, -A-B—X is

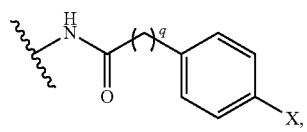

and q is an integer from 0 to 12. In another embodiment of Formula I, -A-B—X is absent. In another embodiment of Formula I, $L_1$ is —$[(CH_2)_n(CO)NH]_p$— wherein p is an integer from 0 to 4, and n is an integer from 1 to 3. In yet another embodiment of Formula I, m is 0. In yet another embodiment of Formula I, $R_1$ and $R_4$ are each chosen independently from halogen, hydroxyl, cyano, $C_1$-$C_6$alkyl, $C_1$-$C_6$alkoxy, $C_1$-$C_6$haloalkyl, and $C_1$-$C_6$haloalkoxy.

In yet another embodiment of Formula I, $R_2$, $R_3$, $R_5$, $R_6$, $R_7$, $R_8$, $R_9$, $R_{10}$, and $R_{11}$ are each hydrogen.

In yet another embodiment of Formula I, $R_1$ and $R_4$ are chosen independently from $C_1$-$C_6$alkyl.

In yet another embodiment of Formula I, $R_1$ and $R_4$ are each methyl.

In a particularly preferred embodiment of Formula I, the compound of Formula I is:

Formula I

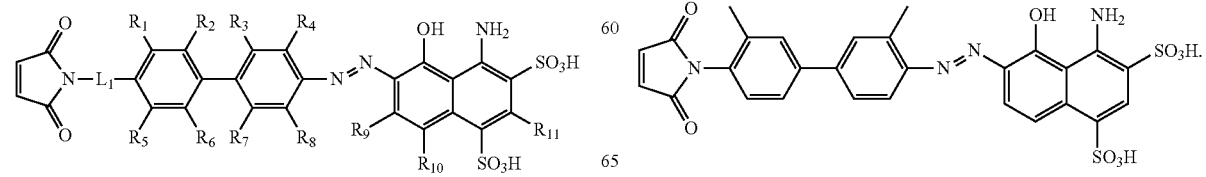

In another particularly preferred embodiment of Formula I, the compound of Formula I is

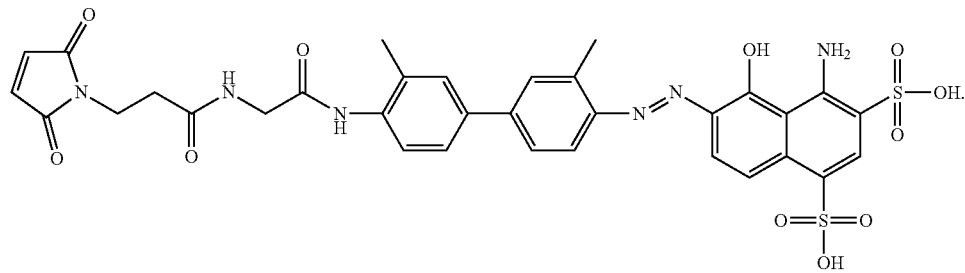 [SMILES: Cc1cc(-c2ccc(NC(=O)CNC(=O)CCN3C(=O)C=CC3=O)c(C)c2)ccc1/N=N/c1ccc2c(S(=O)(=O)O)cc(S(=O)(=O)O)c(N)c2c1O]

In yet another embodiment of Formula I, the compound of Formula I additionally comprises a radionuclide. In yet another embodiment of Formula I, -A-B—X additionally comprises a radionuclide. In yet another embodiment, the radionuclides present in the previous embodiments can be $^{18}F$, $^{76}Br$, $^{124}I$, $^{125}I$, or $^{131}I$, or $^{117}Sn$.

In another aspect, the present invention encompasses chemical conjugates of Evans Blue dye having the compound of Formula II illustrated below, or a pharmaceutically acceptable ester, amide, solvate, or salt thereof, or a salt of such an ester or amide or a solvate of such an ester amide or salt:

Formula II

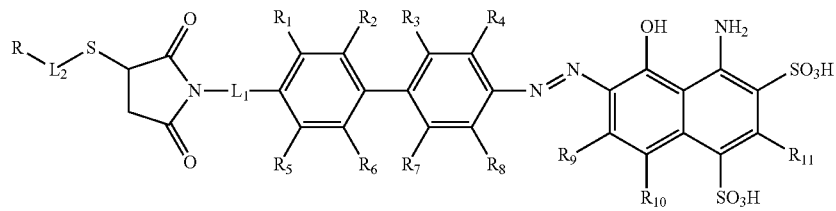

In Formula II, the substituents $R_1$, $R_2$, $R_3$, $R_4$, $R_5$, $R_6$, $R_7$, $R_8$, $R_9$, $R_{10}$, and $R_{11}$ are each chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy.

Formula II may also include a linking group $L_1$ having the structure —$(CH_2)_m$— wherein m is an integer from 0 to 12, wherein each $CH_2$ can be individually replaced with —O—, —NH(CO)—, or —(CO)NH—, providing no two adjacent $CH_2$ groups are replaced, and wherein $L_1$ is optionally substituted with 1 substituent -A-B—X, wherein A is a bond, —NH—, —NH(CO)—, —(CO)NH—, B is $C_{0-12}$alkyl, or phenyl$C_{0-12}$alkyl, and X is a hydrogen, halogen or an Sn derivative.

Formula II may also include a linking group $L_2$ having the structure —$(CH_2)_r$— wherein r is an integer from 0 to 12, wherein each $CH_2$ can be individually replaced with —O—, —NH(CO)—, or —(CO)NH—, providing no two adjacent $CH_2$ groups are replaced. In Formula II, R is a therapeutic compound as explained in more detail below.

In an embodiment of Formula II, -A-B—X is

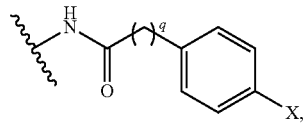

and q is an integer from 0 to 12. In another embodiment of Formula I, -A-B—X is absent. In another embodiment of Formula II, $L_1$ is —$[(CH_2)_n(CO)NH]_p$— wherein p is an integer from 0 to 4, and n is an integer from 1 to 3. In yet another embodiment of Formula II, m is 0. In yet another embodiment of Formula II, r is 0.

In another embodiment of Formula II, $R_1$ and $R_4$ are methyl.

In yet another embodiment of Formula II, $R_2$, $R_3$, $R_5$, $R_6$, $R_7$, $R_8$, $R_9$, $R_{10}$, and $R_{11}$ are hydrogen.

In yet another embodiment of Formula II, m is 0, r is 0, $R_1$ and $R_4$ are methyl and $R_2$, $R_3$, $R_5$, $R_6$, $R_7$, $R_8$, $R_9$, $R_{10}$, and $R_{11}$ are hydrogen.

In Formula II, R is a therapeutic compound. The therapeutic compound may be any compound having therapeutic properties, and may encompass small molecular therapeutic molecules, peptidic drugs, or protein-based therapeutics. Examples of suitable small molecular therapeutic molecules useful in Formula II include, but are not limited to, doxorubicin, paclitaxel, gemcitabine, camptothecin, temozolomide, and the like. Examples of suitable peptidic drugs useful in Formula II include, but are not limited to insulin, GLP-1, Exendin-4, octreotide, bombesin, RGD peptide (arginylglycylaspartic acid), and the like, or a therapeutic fragment thereof. Examples of suitable therapeutic proteins useful in Formula II include, but are not limited to vascular endothelial growth factor (VEGF), interferon (IFN), tumor necrosis factor (TNF), asparaginase, adenosine deaminase, and the like, or a therapeutic fragment thereof. Another example of a useful therapeutic peptide that may be included in the compounds and methods described herein is Exendin (9-39), a 31 amino acid fragment of Exenatide which is useful, for example, in the treatment of post-bariatric hypoglycemia. Preferably, the therapeutic compound R in Formula II is capable of treating or diagnosing diseases or conditions in mammals, and preferably humans. For example, in an embodiment, R is selected for its ability to treat or diagnose cancer or diabetes.

It should be understood that R can be a native therapeutic molecule, or a therapeutically active fragment thereof. Preferably, R contains a sulfhydryl moiety that facilitates conjugation or cross-linking between it and the maleimide moiety of Formula I to form the conjugated complex of Formula II. The active sulfhydryl moiety on the therapeutic compound may be naturally occurring (for example, Cys-40 in Exendin-4), or may be artificially introduced into the therapeutic compound or fragment by methods well known in the art such as amino acid substitution or chemical modification.

In a particularly preferred embodiment of Formula II, the compound of Formula II is:

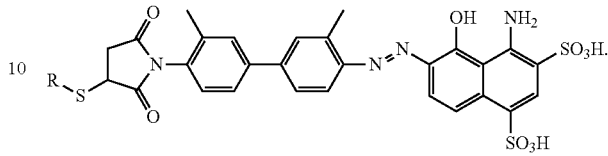

In another particularly preferred embodiment of Formula II, the compound of Formula II is

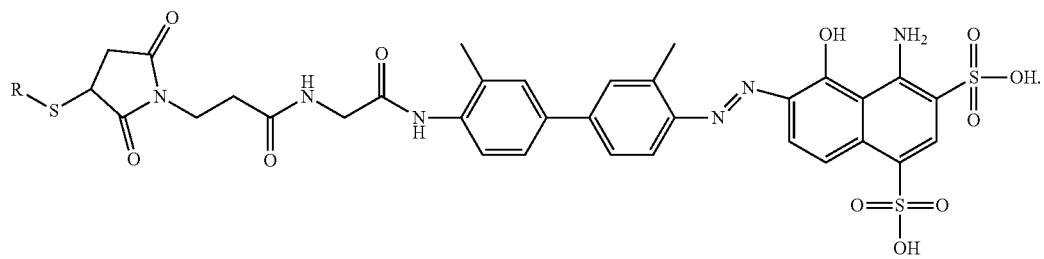

In yet another particularly preferred embodiment of Formula II, the compound of Formula II is conjugated to Exendin-4 through Cys-40:

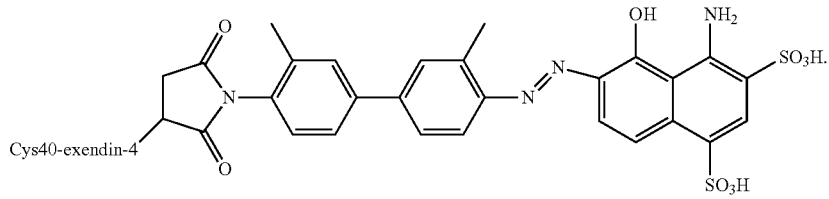

In yet another embodiment of Formula II, the compound of Formula II additionally comprises a radionuclide. In yet another embodiment of Formula II, -A-B—X additionally comprises a radionuclide. In yet another embodiment of Formula II, the radionuclides present in the previous embodiments can be $^{18}F$, $^{76}Br$, $^{124}I$, $^{125}I$, or $^{131}I$, or $^{117}Sn$.

In a particularly preferred embodiment of Formula II, the compound of Formula II is

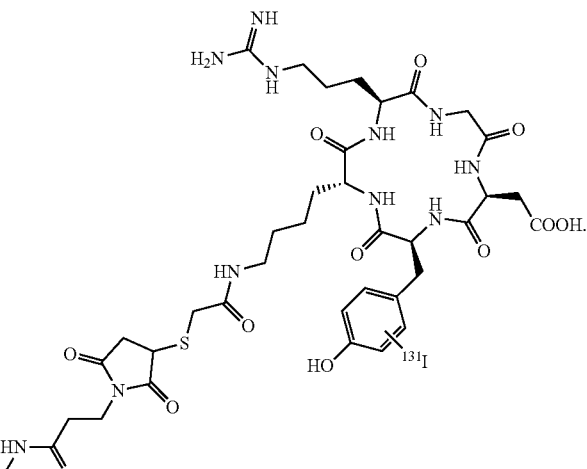
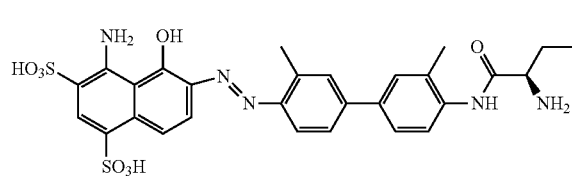

In another particularly preferred embodiment of Formula II, the compound of Formula II is a compound of Formula III, wherein X is a radionuclide which can be $^{18}F$, $^{76}Br$, $^{124}I$, $^{125}I$, $^{131}I$, or a derivative of $^{117m}Sn$. In a particularly preferred embodiment of Formula III, X is $^{131}I$.

pound or pharmaceutically acceptable salt of a compound, such as a compound of Formula II, together with at least one pharmaceutically acceptable carrier. The pharmaceutical composition may contain a compound or salt of Formula II as the only active agent, but is preferably contains at least Formula III

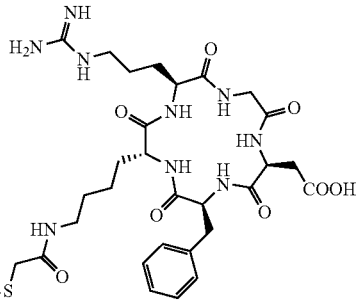
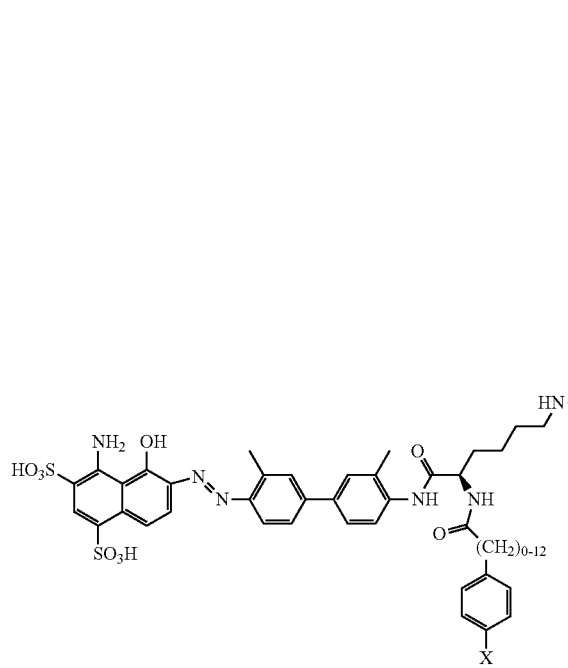

Pharmaceutical Preparations

Compounds disclosed herein can be administered as the neat chemical, but are preferably administered as a pharmaceutical composition. Accordingly, the invention encompasses pharmaceutical compositions comprising a compound or pharmaceutically acceptable salt of a compound, one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula II and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound, such as a compound of Formula II, and an additional active agent. For example the pharmaceutical composition may contain a molar ratio of about 0.5:1, about 1:1, about 2:1, about 3:1 or from about 1.5:1 to about 4:1 of an additional active agent to a compound of Formula II.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula II and usually at least about 5 wt. % of a compound of Formula II. Some embodiments contain from about 25 wt. % to about 50 wt. % or from about 5 wt. % to about 75 wt. % of the compound of Formula II.

Treatment Methods

The compounds of Formula II, as well as pharmaceutical compositions comprising the compounds, are useful for diagnosis or treatment of diseases such as diabetes or cancer. According to the present invention, a method of treating diabetes comprises providing to a patient in need of such treatment a therapeutically effective amount of a compound of Formula II. In an embodiment, the patient is a mammal, and more specifically a human. As will be understood by one skilled in the art, the invention also encompasses methods of treating non-human patients such as companion animals, e.g. cats, dogs, and livestock animals.

A therapeutically effective amount of a pharmaceutical composition is preferably an amount sufficient to reduce or ameliorate the symptoms of a disease or condition. In the case of diabetes for example, a therapeutically effective amount may be an amount sufficient to reduce or ameliorate high blood sugar. A therapeutically effective amount of a compound or pharmaceutical composition described herein will also provide a sufficient concentration of a compound of Formula II when administered to a patient. A sufficient concentration is preferably a concentration of the compound in the patient's body necessary to prevent or combat the disorder. Such an amount may be ascertained experimentally, for example by assaying blood concentration of the compound, or theoretically, by calculating bioavailability.

According to the invention, the methods of treatment disclosed herein include providing certain dosage amounts of a compound of Formula II to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula II may be administered singularly (i.e., sole therapeutic agent of a regime) to treat or prevent diseases and conditions such as diabetes, or may be administered in combination with another active agent. One or more compounds of Formula II may be administered in coordination with a regime of one or more other active agents such as insulin secretagogs.

As will be appreciated by one skilled in the art, the methods of treatment provided herein are also useful for treatment of mammals other than humans, including for veterinary applications such as to treat horses and livestock, e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g. blood, plasma, serum, cellular interstitial fluid, saliva, feces, and urine) and cell and tissue samples of the above subjects will be suitable for use.

In an embodiment, the invention provides a method of treating a diabetes disorder in a patient identified as in need of such treatment, the method comprising providing to the patient an effective amount of a compound of Formula II. The compounds of Formula II provided herein may be administered alone, or in combination with one or more other active agents.

In another embodiment, the method of treating diabetes may additionally comprise administering the compound of Formula II in combination with one or more additional compounds, wherein at least one of the additional compounds is an active agent, to a patient in need of such treatment. The one or more additional compounds may include insulin, exenatide, DPP-4 (dipeptidyl peptidase-4) inhibitors, neuropilin, EGF (epidermal growth factor), INGAP (islet neogenesis associated protein), alpha-1 antitrypsin, anti-inflammatory agents, glulisine, glucagons, local cytokines, modulators of cytokines, anti-apoptotic molecules, aptamers, asparaginase, adenosine deaminase, interferon α2a, interferon α2b, G-CSF (granulocyte colony stimulating factor), growth hormone receptor antagonists, and combinations thereof.

The compositions of the present invention offer the advantage that many small molecules and biologics can be easily modified in one step with high yield and high purity. Due to the relatively strong binding of EB moiety with albumin, the in vivo biodistribution can be easily controlled to adjust the number of EB moieties and linkers. In addition, the relative small size of the EB moiety reduces the likelihood of any interference with the biological function of the drug candidates. The present invention therefore provides an efficient system for developing long lasting and long acting drugs with high efficacy.

EXAMPLES

The present invention is further described in detail by means of the following Examples. All parts and percentages are by weight and all temperatures are degrees Celsius unless explicitly stated otherwise.

Abbreviations

AUC Area Under the Curve
Boc tert-butoxycarbonyl
DCM Dichloromethane
DMF N,N-Dimethylformamide
DMSO Dimethyl Sulfoxide
DTT Dithiothreitol
EDT 1,2-Ethanedithiol
HPLC High Performance Liquid Chromatography
HRMS High Resolution Mass Spectrometry
LC/MS Liquid Chromatography/Mass Spectrometry
NMR Nuclear Magnetic Resonance
NOTA 1,4,7-triazacyclononane-N,N',N"-triacetic acid
PBS Phosphate Buffered Saline
PET Positron Emission Tomography
RPMI Roswell Park Memorial Institute cell media
SFB N-Succinimidyl-4-fluorobenzoate
TAS Thioanisole
TFA Trifluoroacetic acid
THF Tetrahydrofuran General Methods 2-tolidine and 1-amino-naphthol-2,4-disulfonic acid monosodium salt were purchased from TCI America (Portland, Oreg.) and NOTA-NHS was obtained from Macrocyclics (Dallas, Tex.). All other chemicals were purchased from Sigma-Aldrich. Waters 600 high-performance liquid chromatography (HPLC) system with a Waters 996 Photodiode Array Detector (PDA) and an online radioactivity detector (Beckman) using a semi-preparative C-18 HPLC column (XTerra Prep RP18, 10 μm, 7.8×300 mm, Waters) was used for purification of products. Varian BOND ELUT C18 column (100 mg) was used for solid phase extraction. A Perkin Elmer 200 series HPLC pump with a Waters 2487 UV detector and a Bioscan Flow-Count detector using an analytical C-18 HPLC column (XTerra 5 μm, 150×4.6 mm, Waters) was used for analysis labeled compounds. HPLC running a linear gradient starting from 5% A (0.1% TFA in acetonitrile) and 95% B (0.1% TFA in water) for 5 min and increasing to 65% A at 35 min with a flow rate of 5 ml/min for semi-prep HPLC and 1 ml/min for analytical HPLC. Mass spectra were obtained with Waters LC-MS system (Waters, Milford, Mass.) that included an Acquity UPLC system coupled to the Waters Q-Tof Premier high-resolution mass spectrometer. The 68Ge/68Ga generator was purchased from Ithemba Labs (South Africa) and F-18 fluoride was obtained from NIH cyclotron facility.

Example 1: Preparation of Maleimide-EB

To a 100 ml round bottom flask containing 2-tolidine (4.3 g) and methylene chloride (40 ml) was added di-t-butyldicarbonate (4.4 g). The mixture was stirred at room temperature overnight. The reaction was concentrated and the residue was purified by chromatography on silica gel to give 3.2 g of N-Boc-2-tolidine. LC-MS: [MH]$^+$=313.4135 (m/z), calc: 312.1838.

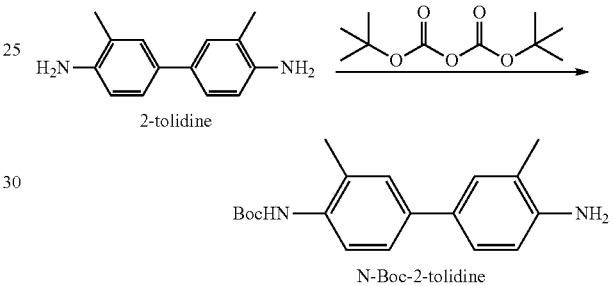

N-Boc-2-tolidine (0.46 g, 1.47 mmol) was dissolved in acetonitrile (10 ml) in a glass vial, was cooled to 0° C., then hydrochloric acid (0.3 M, 15 ml) was added. Cold sodium nitrite solution (0.31 g in 5 ml water) was added dropwise and stirred for 20 min, and the solution turned bright yellow. This solution was added dropwise to another glass vial containing 1-amino-8-naphthol-2,4-disulfonic acid monosodium salt (0.59 g) and sodium bicarbonate (0.49 g) in water (20 ml) at 0° C. The reaction was deemed complete by LC/MS and the reaction was lyophilized without further purification to provide the Boc-EB product. [M-H]$^-$= 541.4425, calc: 542.0930.

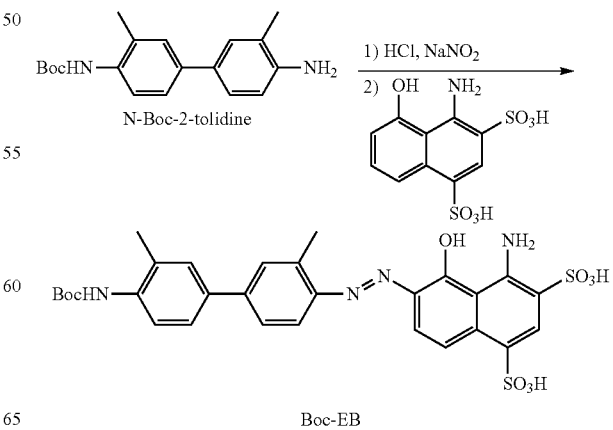

The Boc EB product was added to a solution of 80% TFA, 10% 1,2-ethanedithiol and 10% thioanisole and stirred until reaction was complete. The mixture was diluted with water (100 ml) and loaded on a C-18 chromatography cartridge (3×15 cm). The column was washed with water and then with 80% ethanol to elute the desired product. After evaporation of the solvent in the eluent, 0.6 g of 80% pure product modified EB (MEB) was obtained. A small amount of product was further purified by HPLC. LC-MS: [M-H]⁻= 541.4425, calc: 542.0930.

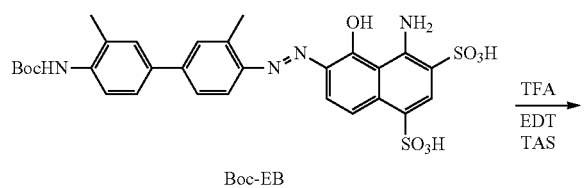

To a solution of MEB (structure IIIa) (30 mg) in methanol (4 ml), DIPEA (50 µl) and maleic anhydride (160 mg) were added, and the reaction was stirred at room temperature for two hours. When the reaction to form intermediate IVa was complete as judged by HPLC, the solvent was evaporated, acetic anhydride (1 ml) was added, and the reaction was heated at 105° C. for 30 min. When LC/MS showed complete conversion to desired product, the mixture was diluted with water (16 ml) and purified on a Waters Xterra C-18 chromatography column running a linear gradient from 5% A (0.1% TFA in acetonitrile) and 95% B (0.1% TFA in water) for 2 min and increasing A to 65%. The desired product was collected and lyophilized to give Maleimide-EB (structure Ia) in a yield of 6.0 mg. LC-MS: [M-H]⁻= 621.5282, calc: 622.0828.

Example 2: Preparation of EB-Exendin-4

To a solution of cys-40-Exendin-4 (6.3 mg) in 3 mL PBS buffer (pH 7.0) was added 2.0 mg of maleimide-EB Ia. The mixture was stirred at room temperature and monitored with HPLC. After the completion of the reaction, the mixture was purified with semi-prep HPLC in 5 injections. The fractions containing the product were collected and lyophilized to give 7.2 mg of desired product, EB-Exendin-4. LC-MS: [MH]⁺=4911.00, calc: 4912.32.

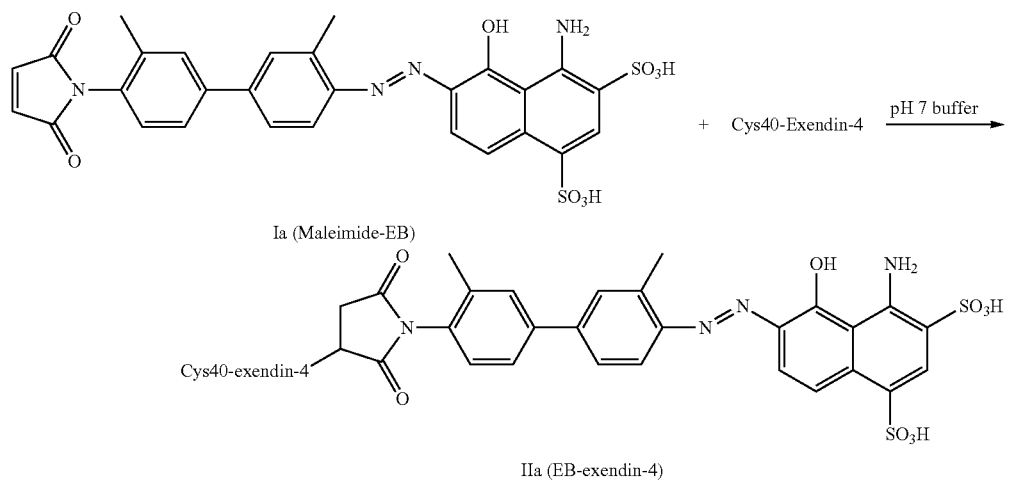

Ia (Maleimide-EB)

IIa (EB-exendin-4)

Example 3: Radiolabeling Exendin-4 and EB-Exendin-4 with F-18 SFB

F-18 SFB (~5 mCi in 0.5 mL methylene chloride) prepared using an automated synthesizer according to the published procedure was transferred to a 1 mL plastic tube and the solvent was evaporated with an argon flow. F-18 SFB in the tube was re-dissolved in 10 μL of acetonitrile and 0.5 mg of Exendin-4 in 0.3 mL 25 mM phosphate buffer (pH 8.5) was added to the tube. The mixture was injected onto the semi-prep HPLC after 10 min reaction at 37° C. The radioactive peak (Rt=23.2 min) was collected and radioactive product trapped on a 100 mg Varian Bond Elut C18 column and washed with 10 mL water. The radioactivity trapped on the $C_{18}$ column was eluted off with 0.3 mL of ethanol with 1 mM HCl. Radiochemical yield of $^{18}$F-Exendin-4: 34%. EB-cys40-Exendin-4 was labeled with similar procedure with a Radiochemical yield of $^{18}$F-EB-Exendin-4 of 28%.

Example 4: Cell Binding Assay

Methods: INS-1 cells (stably transfected cells containing human proinsulin gene) were trypsinized and resuspended in RPMI 1640 medium (Life Technologies, Grand Island, N.Y.). Incubation was conducted with 96-well MultiScreen filter plates (Millipore, Mass.). Each well had a reaction volume of 200 μL containing $2 \times 10^5$ cells, 200 nCi (7.4 kBq) of $^{18}$F-Exendin-4 and 0-500 nM of unlabeled Exendin-4 or EB-Exendin-4. The reaction was incubated for 45 min on a shaker at room temperature. After incubation, cells were washed three times with RPMI medium buffer. Cell bound membranes were dried and isolated. The radioactivity was measured using a gamma counter (1480 Wizard 3, Perkin-Elmer). Binding results were expressed as percent of total counts, $IC_{50}$ values were calculated using Prism software (GraphPad Software Inc., La Jolla, Calif.).

FIG. 1 shows the results of the above cell binding assay of Exendin-4 and EB-Exendin-4 with INS-1 cells using $^{18}$F-Exendin-4 as the radioligand. The $IC_{50}$ values were determined to be 0.21±0.08 nM and 0.18±0.06 nM, respectively. As shown in FIG. 1, compared with Exendin-4, EB-Exendin-4 had similarly high binding affinity for GLP-1R (0.21±0.08 vs. 0.18±0.06 nM), indicating that EB conjugation did not comprise the binding affinity of the Exendin-4 peptide.

Example 5: Small Animal Pet Imaging

Methods: Tumor model establishment: All animal studies were conducted in accordance with the principles and procedures outlined in the Guide for the Care and Use of Laboratory Animals and were approved by the Institutional Animal Care and Use Committee of the Clinical Center, NIH. The tumor models were established by inoculating the right shoulder of 5- to 6-week old female athymic nude mice (Harlan Laboratories) subcutaneously with $5 \times 10^6$ rat insulinoma INS-1 cells in 100 al PBS. The mice underwent PET scans when the tumor volume reached 200-400 $mm^3$ (about 2-3 weeks after inoculation).

Dynamic PET Imaging:

All the PET scans were conducted with an Inveon small-animal PET scanner (Siemens Preclinical Solution). Mice were anesthetized with mixtures of 1 ml/min $O_2$ and 1.5% isoflurane and kept warm with a heating pad thermostat during the imaging. All data acquisitions were initiated immediately before the tracer injections. The duration of a scan was 60 min. A catheter was placed in the tail vein before each scan for tracer administration. About 3.7 MBq (100 μCi) of $^{18}$F-Exendin-4 or $^{18}$F-EB-Exendin-4 was injected through the catheter immediately after the scan was started (n=4 for each tracer). After the 60 min dynamic scan, all mice were scanned at 120 min post injection.

Image Reconstruction and Data Analysis:

The images were reconstructed using a two-dimensional ordered-subset expectation maximization (2D OSEM) algorithm, and no correction was applied for attenuation or scattering. For each scan, regions of interest (ROIs) were drawn over the tumor and major organs using vendor software (ASI Pro 5.2.4.0) on decay-corrected whole-body coronal images. The radioactivity concentrations (accumulation) within the tumors, muscle, liver, and kidneys were obtained from mean pixel values within the multiple ROI volume and then converted to MBq per milliliter per minute using the calibration factor determined for the Inveon PET system. These values were then divided by the administered activity to obtain (assuming a tissue density of 1 g/ml) an image-ROI-derived percent injected dose per gram (% ID/g).

Ex Vivo Biodistribution:

Immediately after PET imaging at 120 min post tracer injection, the tumor-bearing mice were sacrificed and dissected. Blood, tumor, major organs, and tissues were collected and wet-weighed. The radioactivity in the wet whole tissue was measured with a γ-counter (Packard). The results were expressed as percentage of injected dose per gram of tissue (% ID/g) for a group of 4 animals. For each mouse, the radioactivity of the tissue samples was calibrated against a known aliquot of the injected radiotracer and normalized to a body mass of 20 g. Values were expressed as mean±SD (n=4/group).

Figure 2A:
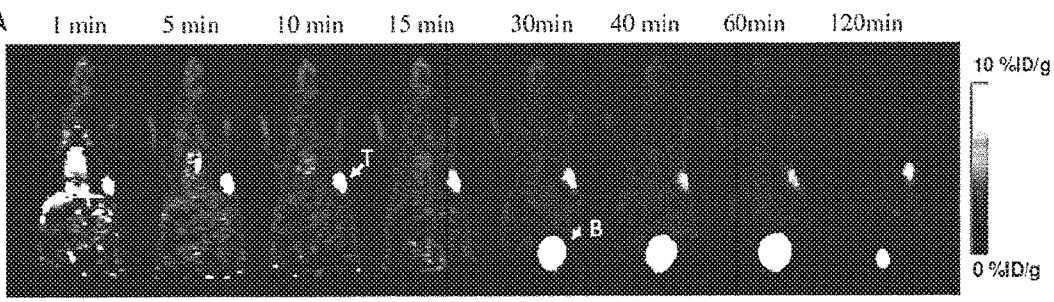
FIG. 2A is a positron emission tomography (PET) scan showing whole body PET images of tumor-bearing mice injected with $^{18}$F-Exendin-4.

FIG. 2A shows whole body PET images (coronal plane) of athymic nude mice bearing INS-tumors on the shoulder at different time points after tail vein injection of 3.7 MBq of $^{18}$F-Exendin-4. The displayed plane was selected to best show the tumor cross section. As shown in FIG. 2A, at early time points (1 min and 5 min), $^{18}$F-Exendin-4 presented an initial distribution in the circulation system, indicated by relatively high tracer accumulation in the heart and liver. The INS-1 tumors were visualized clearly even at 1 min time point. The compound was cleared out very quickly through the urinary tract, demonstrated by the high accumulation of radioactivity in kidneys and bladder. After 60 min, the background signal from other part of the whole body is very low.

Figure 2B:
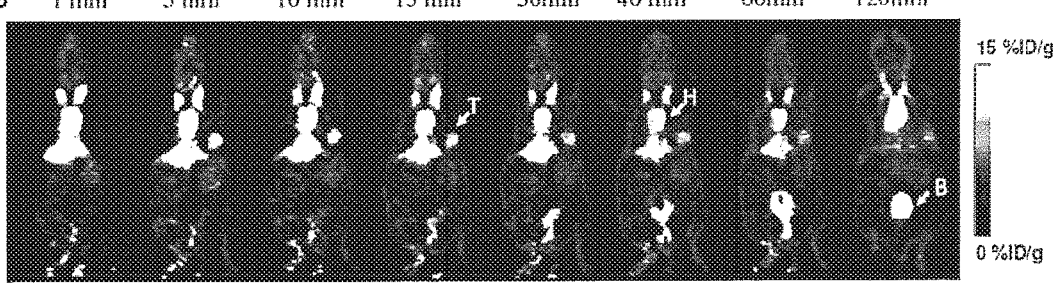
FIG. 2B is a PET scan showing whole body PET images of tumor-bearing mice injected with $^{18}$F-EB-Exendin-4.
Figure 2C:
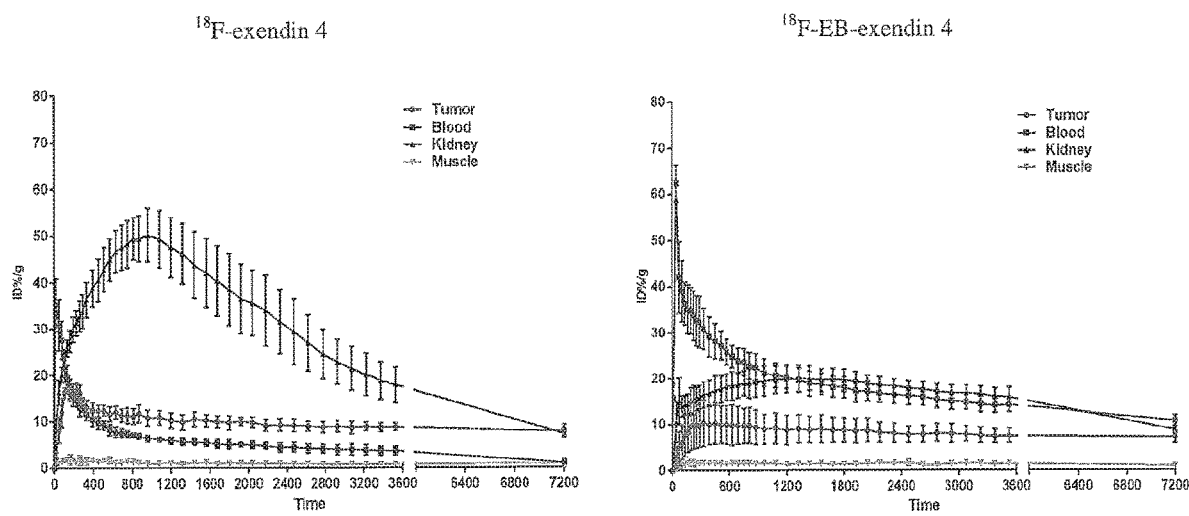
FIG. 2C is a graph showing time activity curves based on the PET images of FIGS. 2A and 2B.

FIG. 2B shows whole body PET images (coronal plane) of athymic nude mice bearing INS-tumors on the shoulder at different time points after tail vein injection of 3.7 MBq of $^{18}$F-EB-Exendin-4. As shown in FIG. 2B, the INS-1 tumors were also visualized clearly with $^{18}$F-EB-Exendin-4 PET. However, the distribution pattern of $^{18}$F-EB-Exendin-4 was dramatically different from that of $^{18}$F-Exendin-4. With the EB moiety, the compound could bind with serum albumin after iv injection. Consequently, very strong radioactive signal can be observed over the heart and major vessels, even at late time points. FIG. 2C shows Time activity curves of tumor, blood, kidney and muscle quantified based on PET images (n=6). T, tumor; H, heart; B, bladder. As can be seen in FIG. 2C, the time-activity curves (TACs) showed the fast clearance of $^{18}$F-Exendin-4, but not $^{18}$F-EB-Exendin-4, through the kidneys. After fitting the TACs over the heart region with two-phase exponential non-linear regression, the $t\alpha_{1/2}$ of EB-Exendin-4 is 0.27 h, which is much longer than that of Exendin-4 ($t\alpha_{1/2}$=0.07 h). The 3 phase half-life ($t\beta_{1/2}$) of EB-Exendin-4 is also much longer than that of Exendin-4 (30.92 h vs. 5.88 h).

Figure 3:
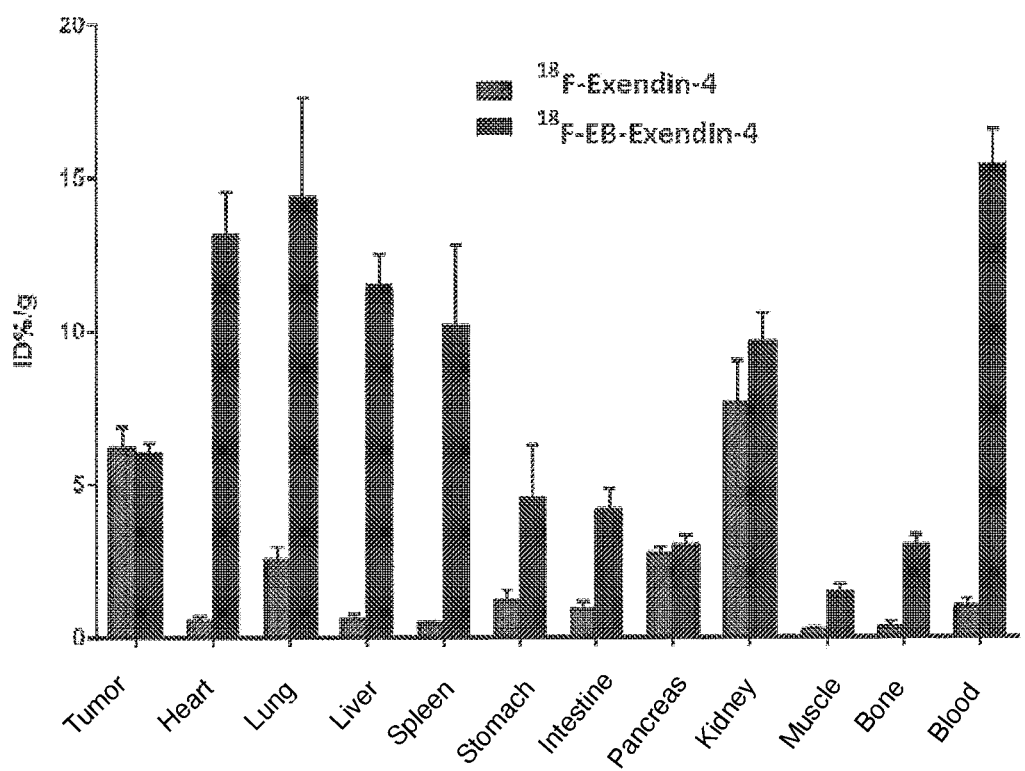
FIG. 3 is a bar graph showing the biodistribution of $^{18}$F-Exendin-4 and $^{18}$F-EB-Exendin-4 in tumor-bearing mice.

In order to further confirm the PET quantification results, the biodistribution of $^{18}$F-Exendin-4 and $^{18}$F-EB-Exendin-4 was evaluated in tumor-bearing athymic nude mice immediately after PET imaging. FIG. 3 shows the biodistribution of $^{18}$F-Exendin-4 and $^{18}$F-EB-Exendin-4 in athymic nude mice bearing subcutaneous INS-1 tumors after PET imaging at the 2 h time point after tracer injection (n=4). As shown in FIG. 3, the INS-1 tumor uptake of both compounds was similar at the 2 h time point (6.20±0.66 vs. 6.06±0.29, P>0.05). In contrast, $^{18}$F-EB-Exendin-4 showed much higher retention in blood circulation and blood enriched organs including liver, spleen, and lung. Especially, the blood concentration of EB-cys40-Exendin-4 is much higher than that of Exendin-4 (15.46±1.13 vs 1.02+0.24% ID/g), indicating the long lasting property of EB-Exendin-4. Quantification of biodistribution at the 2 h time point is shown in Table 1.

TABLE 1

Quantification of biodistribution of $^{18}$F-Exendin-4 and $^{18}$F-EB-Exendin-4 in athymic nude mice bearing subcutaneous INS-1 tumors after PET imaging at the 2 h time point after tracer injection (n = 4).

| Organs | Exendin-4 (ID %/g) | | EB-Exendin-4(ID %/g) | |
|---|---|---|---|---|
| | Mean | SD | Mean | SD |
| Tumor | 6.201989 | 0.659803 | 6.060976 | 0.286350 |
| Heart | 0.558217 | 0.147634 | 13.114690 | 1.408999 |
| Lung | 2.570768 | 0.421053 | 14.382740 | 3.282603 |
| Liver | 0.614344 | 0.164156 | 11.492060 | 1.001602 |
| Spleen | 0.468754 | 0.070510 | 10.186240 | 2.662555 |
| stomach | 1.218335 | 0.339374 | 4.539317 | 1.758315 |
| intestin | 0.958324 | 0.197296 | 4.167974 | 0.705484 |
| pancreas | 2.736785 | 0.224354 | 3.036698 | 0.290930 |
| kidney | 7.684381 | 1.333776 | 9.682252 | 0.912637 |
| Muscle | 0.261806 | 0.090802 | 1.461375 | 0.265874 |
| Bone | 0.380529 | 0.134248 | 3.028530 | 0.309348 |
| Blood | 1.027466 | 0.239521 | 15.456530 | 1.130970 |

Example 6. Efficacy and Pharmacokinetics of EB-Cys40-Exendin-4 in Mice

Type 2 diabetic C57BL/6 db/db mice (males, 6-8 weeks old) were obtained from the Nanjing BioMedical Research Institute of Nanjing University (Nanjing, China). Male Sprague Dawley rats (200-250 g), which were used for pharmacokinetic studies, were purchased from the Experimental Animal Center of Xiamen University (Xiamen, China). Animals were housed in groups of 6-8 under a 12-h light/dark cycle (lights on at 6 a.m.), allowed food and water ad libitum, and acclimatized for 2 weeks. This study was conducted under protocols approved by Animal Care and Use Committee (CCACUCC) of Xiamen University.

Hypoglycemic Efficacies Test in Nonfasted Db/Db Mice.

Hypoglycemic efficacies of Exendin-4 analogues were investigated using an intraperitoneal glucose tolerance test (IPGTT) in male db/db mice (6-7 weeks old). Under non-fasting conditions with free access to food and water, animals received a single s.c. injection of saline, Ex4 or EB-Ex4 (25 nmol/kg body wt.). Blood glucose levels were then monitored using a convenient blood glucose meter (ACCU-CHEK Sensor, Roche Diagnostics Corp., USA). At predetermined times (0, 1, 2, 4, 6, 8, 12, 24, 48, 72, 96 h), blood samples were collected from tail vein of each animal, and blood glucose levels were measured as mentioned above. Hypoglycemic durations to a blood glucose level of <8.35 nM were checked.

In vivo Pharmacokinetics Tests.

The pharmacokinetic profiles of subcutaneously administered Exendin-4 (Ex4) or EB-Exendin-4 (EB-Ex4) (25 nmol/kg body wt.) were evaluated as previously described. The animals were randomly divided into two groups and Ex4 or EB-Ex4 (25 nmol/kg, s.c.) was administered. Blood samples, drawn at predetermined times, were placed in ice-cold polyethylene tubes which contained anticoagulant (heparin solution, 1/100 volume of blood). After that, plasma samples were obtained by centrifugation and stored at −70° C. until required for assay. Amount of Ex4 and EB-Ex4 in plasma were measured by commercial Exendin-4 EIA kits (Phoenixbiotech., USA).

Figure 4:
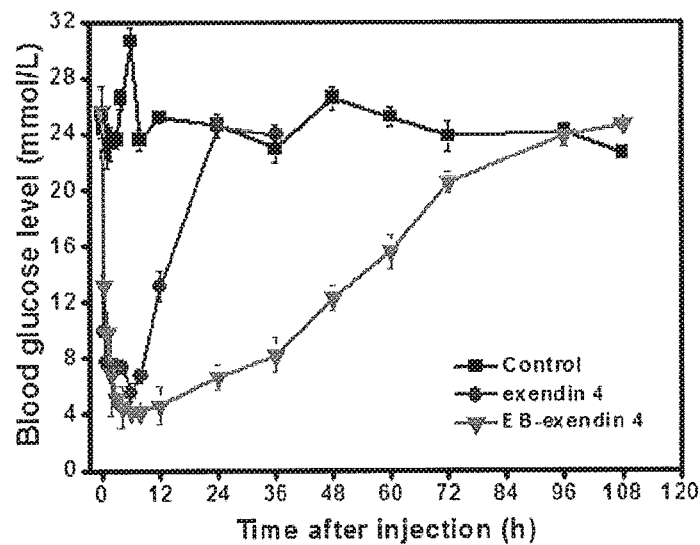
FIG. 4 depicts graphs showing the hypoglycemic efficacies of free Exendin-4 (panel a) and EB-Exendin-4 (panel b)
Figure 4:
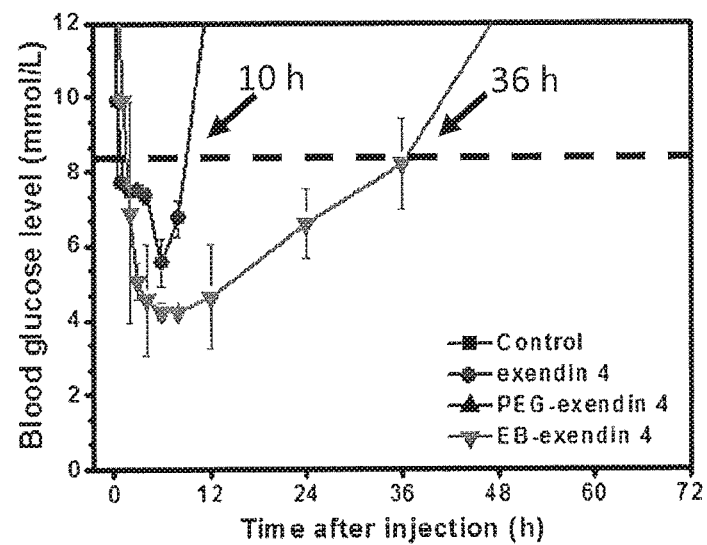
Figure 5:
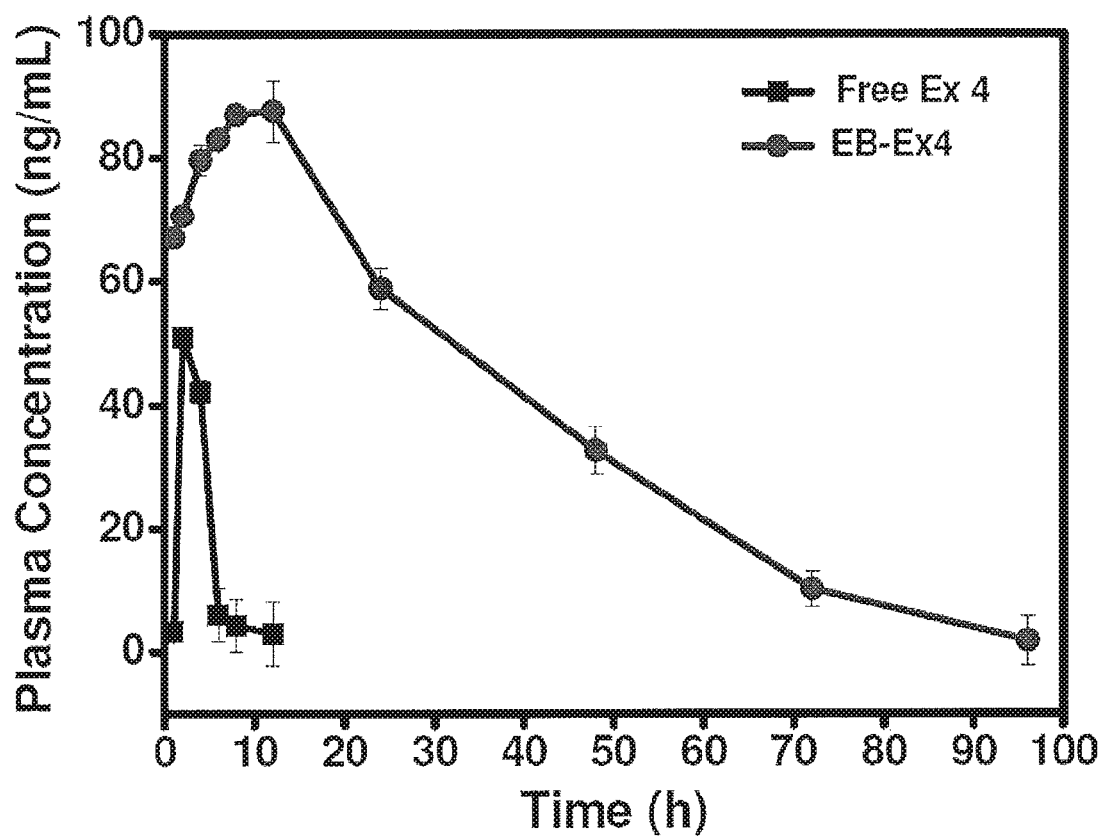
FIG. 5 is a graph showing the pharmacokinetic profiles of free Exendin-4 and EB-Exendin-4 in SD rats.

FIG. 4, panel a, shows the hypoglycemic efficacies of free Exendin-4 and EB-Exendin-4. Data represent three mice and are presented as mean±SDs. FIG. 4, panel b, shows the focused profile of FIG. 4, panel a (0-72 h, 0-12 mmol/L). Times depict hypoglycemic duration rebound to 8.35 mmol/L (normal blood glucose). As shown in the graphs in FIG. 4, the hypoglycemic effects of Exendin-4 and EB-Exendin-4 were examined at 25 nM/kg s.c. in db/db mice. Hypoglycemic duration of EB-Exendin-4 was much greater than Exendin-4, and time required to rebound to a glucose level of 8.35 mmol/L (36 h) was much longer than the 10 h taken in Exendin-4 treated mice. EB-Exendin-4 also showed much improved pharmacokinetic profiles. The blood concentration vs. time curves were plotted for Exendin-4 and EB-Exendin-4. FIG. 5 shows the pharmacokinetic profiles of free Exendin-4 and EB-Exendin-4 in SD rats administered 25 nmol/kg, s.c. Data represent four rats and are presented as mean±SDs. As shown in FIG. 5 and Table 2 below, subcutaneously administered Exendin-4 was rapidly removed from the circulation with a $t_{1/2}$ of 5.16±5.23 h, whereas the $t_{1/2}$ of EB-Exendin-4 was 36 0.28±7.01 h, resulting in a 7-fold greater time than that of native Exendin-4. Furthermore, its $AUC_{inf}$ value (3533.70±236.45 ng/mL*h) was 18 times greater than that of native Exendin-4 (193.21±40.98 ng/mL*h).

TABLE 2

Pharmacokinetic parameters of free Exendin-4 and EB-Exendin-4 after s.c. administration to SD rats.

| Parameter | Free Exendin-4 | EB-Exendin-4 |
| --- | --- | --- |
| C max (ng/mL) | 42.08 ± 1.85 | 87.29 ± 3.71 |
| T max (h) | 4.0 ± 1.32 | 12.3 ± 3.88 |
| $t_{1/2}$ (h) | 5.16 ± 5.23 | 36.28 ± 7.01 |
| $AUC_{inf}$ (ng*h/mL) | 193.21 ± 40.98 | 3533.70 ± 236.45 |

Example 7. Efficacy and Pharmacokinetics of MEB-C3-Cys40-Exendin-4 (Abextide II) in Cynomolgus Monkeys The efficacy and pharmacokinetics of MEB-C3-Cys40-Extendin 4 (Abextide II) was studied in primates. Nine Type 2 diabetic cynomolgus monkeys were separated into 3 groups and each group was injected with one of albiglutide (positive control, 0.9 mg/kg), Abextide II (165 µg/kg), or a saline placebo, as a one-time subcutaneous injection. The structure of Abextide II is shown below.

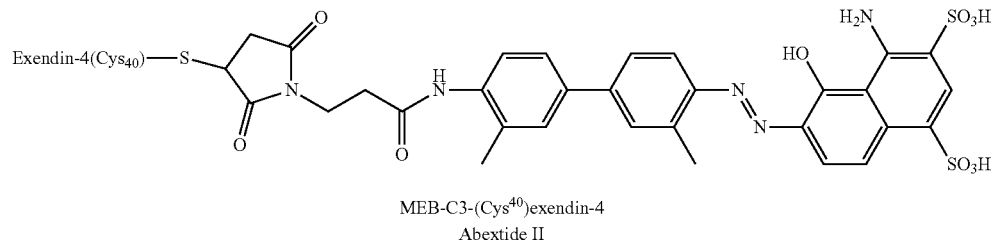

MEB-C3-(Cys40)exendin-4
Abextide II

Plasma glucose levels and body weight were measured, and an intravenous glucose tolerance test (IVGTT) was also performed to assess the efficacy and pharmacokinetics of the compounds. Results are shown in FIGS. 6-9.

Figure 6:
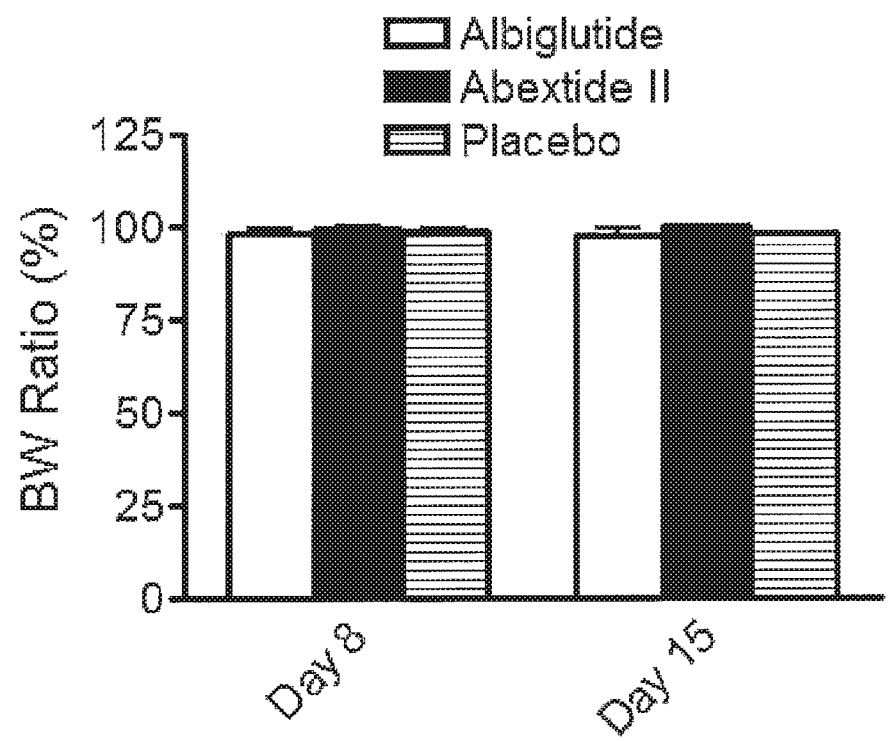
FIG. 6 depicts a graph of weight loss following treatment with Abextide II.

As shown in FIG. 6, at days 8 and 15 after treatment, no body weight loss was found in all groups including Abextide II treated group.

Figure 7A:
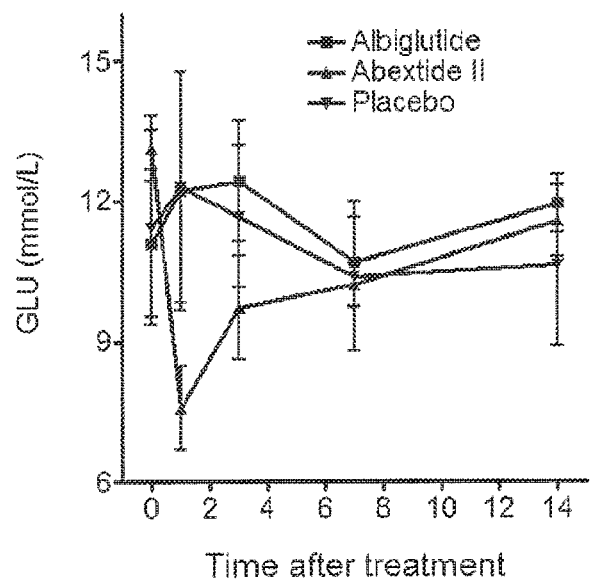
FIG. 7A-7B depict graphs of plasma glucose changes in monkeys.
Figure 7B:
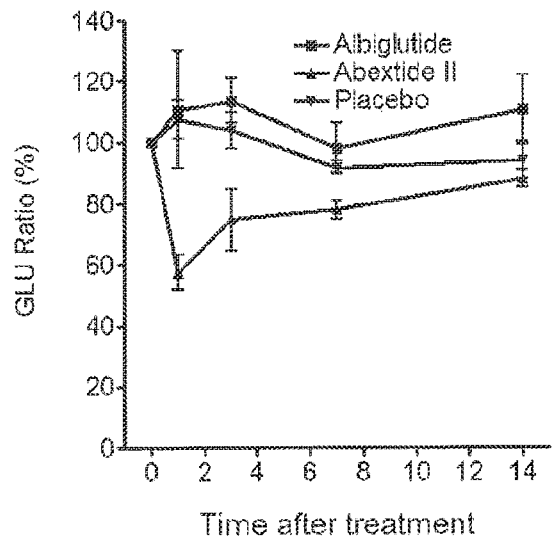

As shown in FIG. 7, panels A and B, at a dose of 165 ug/kg, Abextide II was able to significantly reduce blood glucose level and the effect lasted for about a week. Albiglutide on the other hand, at the clinical dose (0.9 mg/kg) was unable to reduce blood glucose level as compared to the placebo control.

Figure 8A:
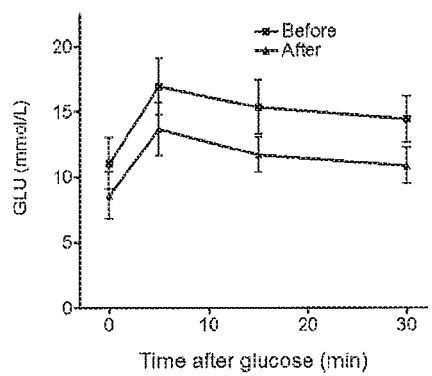
FIG. 8A-C show results of an intravenous glucose tolerance test using albiglutide (panel A), Abextide II (panel B) and placebo (panel C)
Figure 8B:
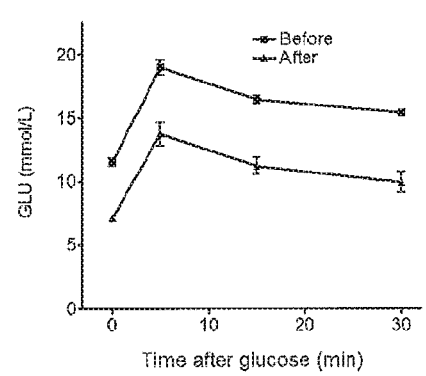
Figure 8C:
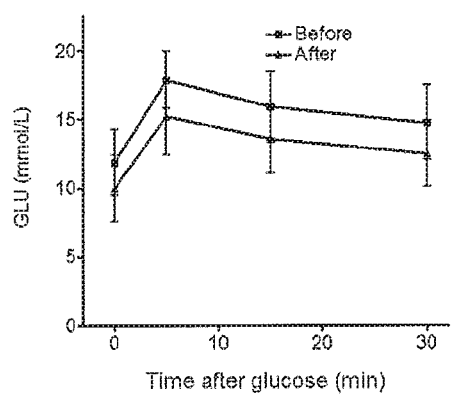
Figure 9:
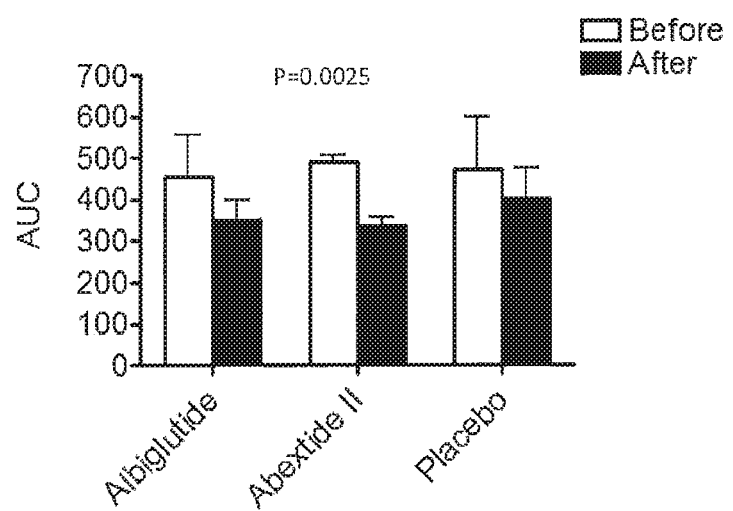
FIG. 9 shows results of an intravenous glucose tolerance test.

Intravenous glucose tolerance test was performed on all animals one week before (baseline) and 2 hours after treatment. As shown in FIG. 8, panels A (Albiglutide), B (Abextide II), and C (placebo), compared with placebo and Albiglutide groups, the monkeys received Abextide II treatment showed more tolerance to glucose. The areas under curve (AUCs) of the plasma glucose level at 0, 5, 15 and 30 min were calculated to quantify IVGTT. As shown in FIG. 9, after Abextide II treatment, the monkeys showed significantly lower area under curve (AUC) than the baseline before treatment. Conversely, significant differences were not observed in placebo and Albuglutide treated groups.

What is claimed is:

1. A compound of Formula I or a pharmaceutically acceptable ester, amide, solvate, or salt thereof, or a salt of such an ester or amide or a solvate of such an ester, amide, or salt, Formula I

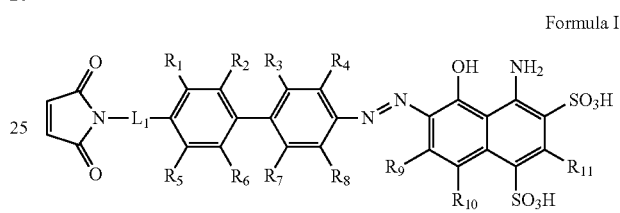

wherein:
$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy; and
$L_1$ is —$(CH_2)_m$— wherein m is an integer from 0 to 12, wherein each $CH_2$ can be individually replaced with —O—, —NH(CO)—, or —(CO)NH—, providing no two adjacent $CH_2$ groups are replaced, and wherein $L_1$ is optionally substituted with 1 substituent -A-B—X, wherein A is a bond, —NH—, —NH(CO)—, —(CO)NH—, B is $C_{0-12}$alkyl, or phenyl$C_{0-12}$alkyl, and X is a hydrogen, halogen or an Sn derivative, and wherein when m is 0, the compound additionally comprises a radionuclide.

2. The compound of claim 1, wherein -A-B—X is

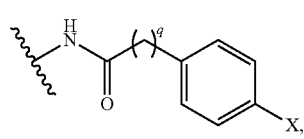

and q is an integer from 0 to 12.

3. The compound of claim 1, wherein $L_1$ is —[(CH$_2$)$_n$(CO)NH]$_p$— wherein p is an integer from 0 to 4, and n is an integer from 1 to 3.

4. The compound of claim 3, wherein m is 0.

5. The compound of claim 1, wherein $R_1$ and $R_4$ are chosen independently from halogen, hydroxyl, cyano, $C_1$-$C_6$alkoxy, $C_1$-$C_6$haloalkyl, and $C_1$-$C_6$haloalkoxy.

6. The compound of claim 1, wherein $R_2$, $R_3$, $R_5$, $R_6$, $R_7$, $R_8$, $R_9$, $R_{10}$, and $R_{11}$ are each hydrogen.

7. The compound of claim 3, wherein $R_1$ and $R_4$ are chosen independently from $C_1$-$C_6$alkyl.

8. The compound of claim 5, wherein $R_1$ and $R_4$ are each methyl.

9. The compound of claim 1, wherein the compound of Formula I is:

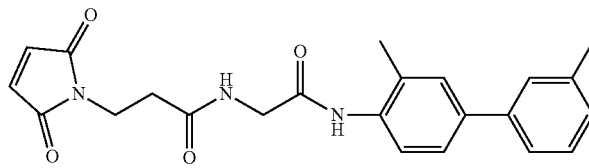

10. The compound of claim 1, wherein -A-B—X additionally comprises a radionuclide.

11. The compound of claim 1, wherein the radionuclide is $^{18}$F, $^{76}$Br, $^{124}$I, $^{125}$I, or $^{131}$I, or $^{117m}$Sn.

12. A compound of Formula II or a pharmaceutically acceptable ester, amide, solvate, or salt thereof, or a salt of such an ester or amide or a solvate of such an ester amide or salt,

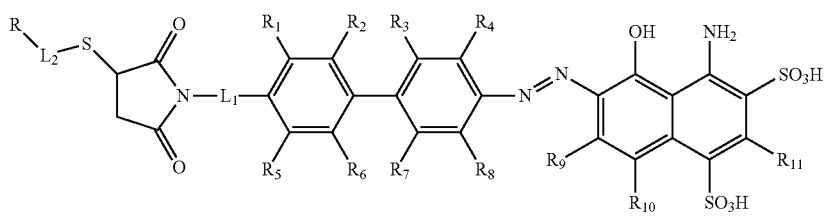

Formula II wherein:
$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkoxy, $C_1$-$C_6$haloalkyl, and $C_1$-$C_6$haloalkoxy;
$L_1$ is —(CH$_2$)$_m$— wherein m is an integer from 0 to 12, wherein each CH$_2$ can be individually replaced with —O—, —NH(CO)—, or —(CO)NH—, providing no two adjacent CH$_2$ groups are replaced, and wherein $L_1$ is optionally substituted with 1 substituent which is -A-B—X, wherein A is a bond, —NH—, —NH(CO)—, —(CO)NH—, B is $C_{0-12}$alkyl, or phenyl$C_{0-12}$alkyl, and X is a hydrogen, halogen or an Sn derivative;
$L_2$ is —(CH$_2$)$_r$— wherein r is an integer from 0 to 12, wherein each CH$_2$ can be individually replaced with —O—, —NH(CO)—, or —(CO)NH—, providing no two adjacent CH$_2$ groups are replaced; and
R is a therapeutic compound.

13. The compound of claim 12, wherein -A-B—X is

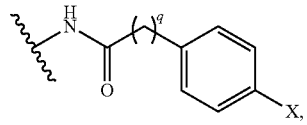

and q is an integer from 0 to 12.

14. The compound of claim 12, wherein $L_1$ is —[(CH$_2$)$_n$(CO)NH]$_p$— wherein p is an integer from 0 to 4, and n is an integer from 1 to 3.

15. The compound of claim 12, wherein m is 0.

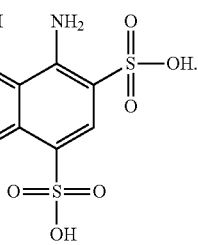

16. The compound of claim 12 wherein m is 0, r is 0, $R_1$ and $R_4$ are each methyl, and $R_2$, $R_3$, $R_5$, $R_6$, $R_7$, $R_8$, $R_9$, $R_{10}$, and $R_{11}$ are each hydrogen.

17. The compound of claim 12, wherein R is a therapeutic protein or peptide.

18. The compound of claim 17, wherein R is selected from insulin, GLP-1, Exendin-4, exendin (9-39), octreotide, bombesin, RGD peptide (arginylglycylaspartic acid), vascular endothelial growth factor (VEGF), interferon (IFN), tumor necrosis factor (TNF), asparaginase, adenosine deaminase, and the like, or a therapeutic fragment thereof.

19. The compound of claim 12, wherein R is selected from doxorubicin, paclitaxel, gemcitabine, camptothecin, and temozolomide.

20. The compound of claim 12 wherein R treats or diagnoses diabetes or cancer.

21. The compound of claim 20 wherein R treats or diagnoses diabetes.

22. The compound of claim 12, wherein the compound is

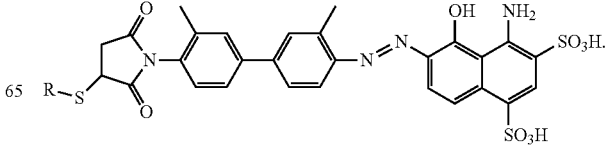

23. The compound of claim 12, wherein the compound is

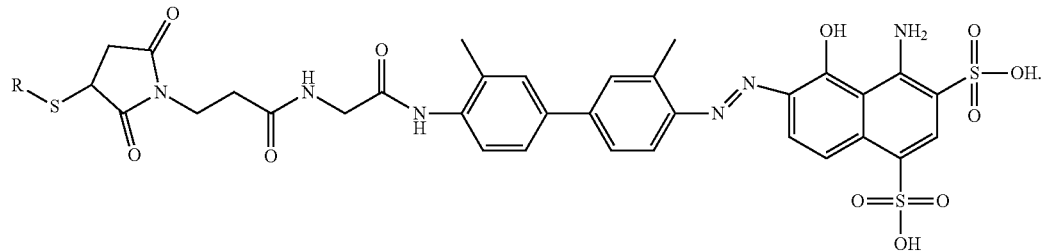

24. The compound of claim 12, wherein the compound is

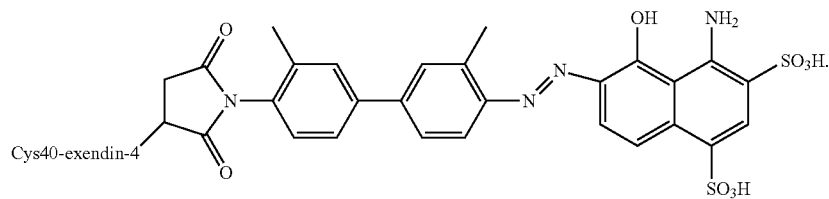

25. The compound of claim 12, additionally comprising a radionuclide.

26. The compound of claim 12, wherein either -A-B—X or R additionally comprises a radionuclide.

27. The compound of claim 25, wherein the radionuclide is $^{18}F$, $^{76}Br$, $^{124}I$, $^{125}I$, or $^{131}I$, or $^{117m}Sn$.

28. The compound of claim 26, wherein the compound is

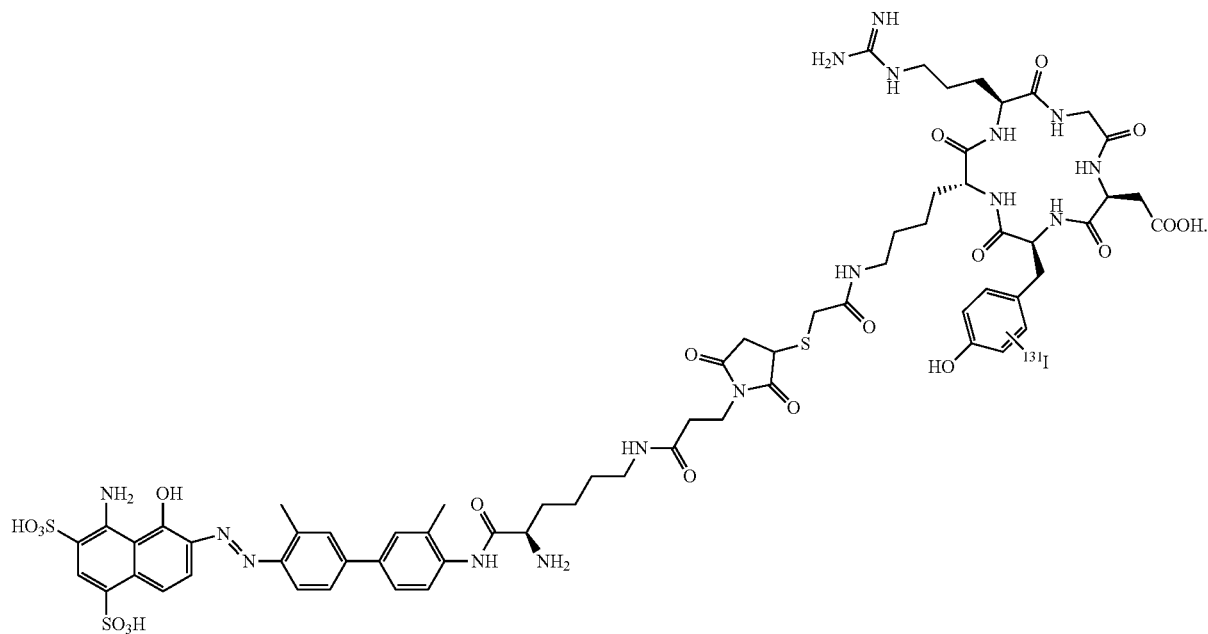

29. The compound of claim 26, wherein the compound is a compound of Formula III

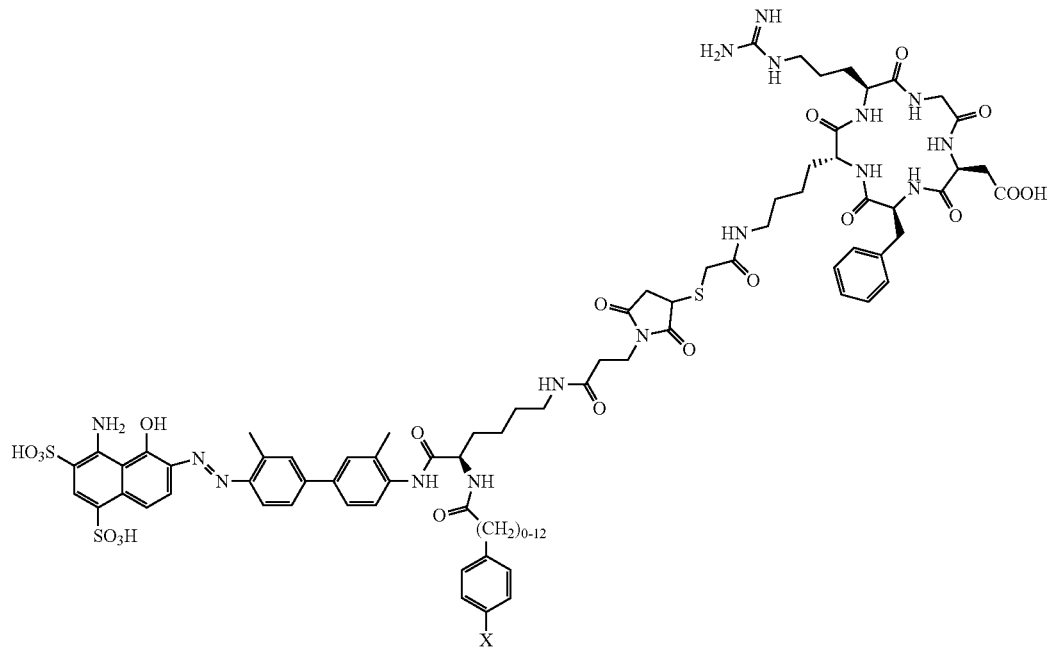

Formula III wherein X is $^{18}$F, $^{76}$Br, $^{124}$I, $^{125}$I, $^{131}$I, or a derivative of $^{117m}$Sn.

30. A pharmaceutical composition comprising the compound of Formula II together with a pharmaceutically acceptable carrier.

31. The composition of claim 30, wherein the pharmaceutically acceptable carrier is selected from binders, buffering agents, coloring agents, diluents, disintegrants, emulsifiers, flavorants, glidants, lubricants, preservatives, stabilizers, surfactants, tableting agents, and wetting agents, and combinations thereof.

32. A method of treating or diagnosing diabetes in a mammal, comprising administering to said mammal a therapeutically effective amount of a compound of Formula II as defined in claim 12, optionally in combination with one or more additional active ingredients.

33. The method of claim 32, wherein the one or more additional active ingredients are selected from insulin, exenatide, dipeptidyl peptidase-4 inhibitors, neuropilin, epidermal growth factor, islet neogenesis associated protein, alpha-1 antitrypsin, anti-inflammatory agents, glulisine, glucagons, local cytokines, modulators of cytokines, anti-apoptotic molecules, aptamers, asparaginase, adenosine deaminase, interferon α2a, interferon α2b, granulocyte colony stimulating factor, growth hormone receptor antagonists, and combinations thereof.

* * * * *